(12) United States Patent
Dos Santos et al.

(10) Patent No.: US 8,338,474 B2
(45) Date of Patent: Dec. 25, 2012

(54) USE OF PHTHALIMIDE AND/OR SULPHONAMIDE DERIVATIVES IN THE TREATMENT OF DISEASES WHICH REQUIRE REDUCING THE TNF-α LEVELS AND AN EXOGENOUS SOURCE OF NITRIC OXIDE, PHTHALIMIDE DERIVATIVES, SULPHONAMIDE DERIVATIVES, AND A METHOD FOR OBTAINING A SULPHONAMIDE DERIVATIVE

(76) Inventors: Jean Leandro Dos Santos, em Franca (BR); Chin Chung Man, em Araraquara (BR); Lídia Moreira Lima, Rio de Janeiro (BR); Fernando Ferreira Costa, em Campinas (BR); Carolina Lanaro, em Campinas (BR)

( * ) Notice: Subject to any disclaimer, the term of this patent is extended or adjusted under 35 U.S.C. 154(b) by 0 days.

(21) Appl. No.: 13/404,777

(22) Filed: Feb. 24, 2012

(65) Prior Publication Data
US 2012/0245364 A1    Sep. 27, 2012

Related U.S. Application Data

(62) Division of application No. 12/747,589, filed as application No. PCT/BR2008/000386 on Dec. 12, 2008.

(30) Foreign Application Priority Data

Dec. 12, 2007 (BR) ..................................... 0705396

(51) Int. Cl.
*A61K 31/4035* (2006.01)
*C07D 209/48* (2006.01)
*C07C 311/48* (2006.01)
*A61P 7/06* (2006.01)
*A61P 29/00* (2006.01)

(52) U.S. Cl. ........... 514/417; 548/476; 548/477; 564/86

(58) Field of Classification Search ................... None
See application file for complete search history.

(56) References Cited

OTHER PUBLICATIONS

Flamigni et al., caplus an 2007:71758.*

* cited by examiner

*Primary Examiner* — Sun Jae Loewe
(74) *Attorney, Agent, or Firm* — Nath, Goldberg & Meyer; Tanya E. Harkins

(57) ABSTRACT

Preparation and use of phthalimide and/or sulphonamide derivatives with nitric oxide donor properties, having activities in increasing gamma-globin gene expression and anti-inflammatory and analgesic activities, effective in the treatment of hematologic diseases which require reducing the TNF-α levels and an exogenous source of nitric oxide, such as sickle-cell disease. The functionalized phthalimide derivatives are designed from the prototypes thalidomide and hydroxyurea.

1 Claim, 5 Drawing Sheets

USE OF PHTHALIMIDE AND/OR SULPHONAMIDE DERIVATIVES IN THE TREATMENT OF DISEASES WHICH REQUIRE REDUCING THE TNF-α LEVELS AND AN EXOGENOUS SOURCE OF NITRIC OXIDE, PHTHALIMIDE DERIVATIVES, SULPHONAMIDE DERIVATIVES, AND A METHOD FOR OBTAINING A SULPHONAMIDE DERIVATIVE

This is a Divisional Application filed under 35 U.S.C. §120 as a division of U.S. patent application Ser. No. 12/747,589, filed on Sep. 7, 2010, which is a National Phase Application filed under 35 U.S.C. §371 as a national stage of PCT/BR2008/000386, filed on Dec. 12, 2008, an application claiming the benefit under 35 U.S.C. §119 of Brazilian Application No. PI 0705396-7, filed on Dec. 12, 2007, the content of each of which is hereby incorporated by reference in their entirety.

The present invention describes the use of phthalimide derivatives with nitric oxide donor properties, which have important activities in increasing the gamma-globin gene expression and anti-inflammatory and analgesic activities, effective in the treatment of hematologic diseases which require reduced TNF-α levels and an exogenous source of nitric oxide. More particularly, the present invention describes the use of such phthalimide derivatives for the treatment of sickle-cell disease.

The Sequence Listing submitted in text format (.txt) on Jun. 14, 2012, named "30927UB_Sequence_Listing_06122012.txt" (created on Jun. 12, 2012, 3 KB), is incorporated herein by reference.

DESCRIPTION OF THE PRIOR ART

The sickle-cell disease is the most prevalent hematologic genetic disease known, and is characterized by a point mutation in the β-globin gene, more specifically a single nucleotide change (GTG into GAG) in the sixth codon of the β-globin gene, resulting in the substitution of a glutamic acid with valine on the surface of the β-globin chain variant ($β^S$-globin) (SAFO, M. K et al. J. Med. Chem. v. 47, pp. 4665-4676, 2004).

The substitution of glutamate with a valine has major consequences on the three-dimensional structure of hemoglobin. Glutamic acid is negatively-charged and valine is a neutral amino acid, thereby allowing the approximation of hemoglobin molecules, and, consequently, the polymerization, when deoxygenized. In the deoxy conformation of sickle-cell hemoglobin (Hb S), valine, which is present in the chain, carries out hydrophobic interactions with the pocket, comprised of hydrophobic amino acids, from a neighboring Hb S molecule, which is not possible in the oxygenated state of hemoglobin, since the hydrophobic pocket is inaccessible in this condition (ADACHI, K. et al. J. Biol. Chem. v. 263, n. 12, pp. 5607-5610, 1988).

These interactions lead to the polymerization of deoxy-Hb S at low oxygen pressures, a typical situation of capillary beds in metabolically-active tissues (AVILA, C. M. et al. Bioorg. Med. Chem. v. 14, pp. 6874-6885, 2006).

The polymerization of Hb S is the central process of vasoocclusion, a characteristic of the sickle-cell disease (BUNN, H. F. N Engl J Med v. 337, pp. 762-769, 1997; KAUL D. K. et al. Blood Rev. v. 10, pp. 29-44, 1996; a) FERRONE, F. A. et al. J. Mol. Biol. v. 183, pp. 591-610, 1985. b) FERRONE, F. et al. J. Mol. Biol. v. 183, pp. 611-631, 1985; SAMUEL, R. E., et al. Blood. v. 82, pp. 3474-3481, 1993).

Due to the intracellular polymerization of hemoglobin, on account of the oxygenation-deoxygenation cycles, the cells containing Hb S take on a sickle shape.

The sickling of red blood cells is associated with the reversible changes of the membrane. With repeated sickling/desickling cycles, the aberrations in the membrane function and structure become increasingly pronounced, culminating in the membrane being fixed in the sickled shape (LEE, G. R. et al. Vol. I Manole, 1998, pp. 1161-1163.)

The sickle red blood cells showed a normal adherence to the vascular endothelium, monocyte, and macrophages (DUITS, A. J. et al. Clin Immunol Immunopathol v. 81, pp. 96-98, 1996; OKPALA, I. et al. J. Eur. J. Haematol. v. 69, pp. 135-144, 2002.)

This property of the sickle blood is given by the deformable sickle cells, but not by the irreversibly sickled cells, perhaps because the rigid cells are not able to form multiple surface contacts with the endothelial cells. This fact denotes a strong positive correlation with the frequency and severity of the pain crises. The turbulence areas in the capillaries are the prevailing sites for adherence.

Vascular occlusion is the main event responsible for the clinical picture of sickle-cell disease, being the cause of pain crises and organ failure. Vaso-occlusive crises initiate at the venular microcirculation, as the sickle cells become trapped. The primary event that is critical for vaso-occlusion includes the adhesion of red blood cells (reticulocytes and deformed dense cells) to the venular endothelium. This adhesion leads to the formation of heterocellular aggregates (white blood cells and sickle cells), which also contribute to obstruction, resulting in local hypoxia, increase on formation of Hb S polymers, and propagation of the occlusion of the neighboring vasculature. Neutrophil transmigrations through endothelial gap junctions increase the inflammation in the microvasculature (OKPALA, I. et al. Eur. J. Haematol. v. 69, pp. 135-144, 2002.; OKPALA, I. Blood Rev. v. 18, pp. 65-73, 2004).

Sickle red blood cell masses repeatedly clog the vessels of the microcirculation, leading to painful vascular occlusion crises. 5% to 10% among children or young adults with sickle-sell disease show, owing to the clogging of the microcirculation vessels, symptomatic pictures of stroke, effusion or hemorrhage resulting from stenosis or aneurismal dilatation of important cerebral arteries.

It has been reported that the increase of fetal hemoglobin is beneficial to patients with sickle-cell disease, increasing its survival and reducing pain episodes (CHARACHE, S. et al. Blood. v. 79, pp. 2555-2565, 1992).

Recently it has been reported that patients with sickle-cell disease show a significant increase on the circulating levels of cytokines, including the tumor necrosis factor-alpha (MALAVÉ, I. et al. Acta Haematol. v. 90, pp. 172-176, 1993; FRANCIS, R. Jr., et al. J. Natl. Med. Assoc. v. 84: 611-615, 1992.; BUCHANAN et al. Hematology. pp. 35-47, 2004), the increased expression of which is directly associated with different pathologies of inflammatory origin (MAKHATADZE, N. J. Hum. Immunol. v. 59, pp. 571-579, 1998).

TNF-α exerts pro-inflammatory effects, increasing the chemiotactic properties, the adherence of neutrophils to the vascular endothelium, due to the increase of adhesion molecules, stimulating the production of free radicals and the synthesis of other inflammatory mediators, such as IL-1 and PGE2. TNF-α also induces changes on the coagulation and anticoagulation properties and increases the hepatic synthesis of some acute-phase reagents. Furthermore, it is an important mediator of septic syndrome and endotoxic shock, being able to suppress the biosynthesis of lipoprotein lipases and lipogenic enzymes in adipose tissue, impairing the storage of lipids on adipocytes.

The ability of TNF-α to change the anticoagulation properties of the vascular endothelium and to induce the procoagulation activity on the cellular surface of endothelium, stimulating the production of the platelet-activating factor (PAF), and increasing the leukocyte adhesion to the vascular endothelium cells, results in a increase of the resistance to the blood flow, making circulation difficult and, thus, aggravating the microvascular stasis and the deoxygenation of Hb S.

Accordingly, an increase on the TNF-α blood levels in patients with sickle-cell disease may aggravate vaso-occlusive crises and also lead to the occurrence of infectious and inflammatory episodes (MALAVÉ, I. et al. Acta Haematol. v. 90, pp. 172-176, 1993).

In fact, Malavé et al (MALAVÉ, I. et al. Acta Haematol. v. 90, pp. 172-176, 1993), reported an interesting inverse correlation between the percentage of fetal hemoglobin (Hb F) and the serum concentration of TNF-α. These authors showed that patients having high plasma levels of TNF-α exhibit a consequent reduction on Hb F levels. Taking into account that Hb F has a beneficial effect, improving the tissue oxygenation and reducing the polymerization of Hb S, such inverse correlation increases the risk of strokes concurrently with symptoms associated with sickle-cell disease. In addition, TNF-α has a major role on peripheral hyperalgesia, and its inhibition has been associated with the reduction of chronic and acute pain, which accounts for the analgesic effect of thalidomide, the first anti-TNF-α drug introduced in therapeutics (RIBEIRO, R. A. et al. Eur. J. Pharmacol., v. 391, pp. 97-103, 2000).

For these reasons, the inhibition of TNF-α has been shown as an important strategy for preventing vascular and inflammatory complications related with sickle-cell disease.

Various substances have been reported to have direct action on the inhibition of TNF-α. These substances include tumor necrosis factor-alpha converting enzyme (TACE) inhibitors, neutralizing antibodies (infliximab), and drugs structurally related with thalidomide.

Many laboratories and research groups have been reported the anti-inflammatory and immunomodulatory properties of thalidomide, demonstrating its therapeutic potential against the treatment of pathologies such as multiple myeloma, cachexia, tuberculosis, arthritis, among others (MIYACHI, H. et al. Bioorg. Med. Chem. v. 5, n. 11, pp. 2095-2102, 1997.)

In this regard, the development of new thalidomide analogs, containing the main pharmacophores for the inhibitory activity of TNF, and free of toxicophoric moieties, responsible for the teratogenicity, constitutes a unique aim for the development of new therapeutic possibilities in the treatment of pathologies associated with or aggravated by the increase on the TNF plasma levels, as in the case of sickle-cell disease.

Nevertheless, there is no specific treatment for sickle-cell disease so far. The treatment of this genetic disease is based on the use of drugs which minimize or fight against the symptomatology of sickle-cell disease. Drugs which are useful to the symptomatic treatment available in the market include desferrioxamine (Desferal®), anti-pneumococcal vaccines, prophylactic penicillin, folic acid (daily doses), and hydroxyurea (Hydrea®).

Hydroxyurea (HU) is a known inhibitor of the synthesis of ribonucleotide reductase, an enzyme responsible for converting ribonucleotides into deoxyribonucleotides, interfering with DNA synthesis, and thus, limits the DNA synthesis (YARBRO, J. M. Semin. Oncol. v. 19, pp. 1-10, 1992; HANFT, V. N. et al. Blood. v. 95, n. 11, 3589-3593, 2000).

Although HU is the main drug available for the treatment of sickle-cell disease approved by the Food and Drug Administration (FDA) agency, various adverse effects are associated with its prolonged use, many of which are due to its ability to interrupt the cell cycle in S and G1 phases (BUCHANAN, G. R. et al. Hematology pp. 35-47, 2004; STUART, M. J. and NAGEL, R. L. Lancet. v. 364, pp. 1343-1360, 2004.), which actions characterize it as a cytotoxic and antineoplastic agent.

Recent studies have showed that therapy with hydroxyurea (HU) reduces deaths associated with sickle-cell disease by 40%. The therapeutic benefit of HU is based on the increase of the levels of fetal hemoglobin (Hb F), a genetically distinct hemoglobin that inhibits the polymerization of deoxygenated sickle-cell hemoglobin (Hb S), preventing or hindering the occurrence of symptoms related with this pathology (STEINBERG, M. H. et al. JAMA, v. 289, pp. 1645-1651, 2003; CHARACHE, S. et al., Medicine v. 75, pp. 300-326, 1996).

Besides inhibiting the ribonucleotide reductase, HU also exerts its action mechanism as a nitric oxide (NO) donator drug, an important mediator in maintaining the normal blood flow and pressure. It is known that HU reacts with oxy- and deoxyhemoglobin to form methemoglobin, which then reacts with another HU molecule in order to form iron-nitrosyl-hemoglobin (HbNO). The formation of HbNO involves a number of reactions of the hydroxylamine moiety in order to form NO(COKIC, V. P. et al. Blood. v. 108, n. 1. pp. 184-191, 2006).

The benefit of nitric oxide (NO) in the treatment of sickle-cell disease is based on its ability to stimulate the production of fetal hemoglobin (Hb F) through the soluble guanylate cyclase (sGC) pathway. The activation of sGC increases the expression of γ-globin in erythroleukemic cells and primary human erythroblasts. The inhibition of sGC prevents this increase, which suggests that the sGC pathway regulates the expression of γ-globin, and consequently, the synthesis of fetal hemoglobin (Hb F). Works have been demonstrating this hypothesis, showing that HU activates sGC and also induces the expression of mRNA γ-globin, increasing the levels of fetal hemoglobin (Hb F) in K562 erythroleukemic cells and human progenitor cells (CONRAN, N. et al. Br. J. Haematol. v. 124, pp. 547-554. 2004).

These results suggest that the induction of Hb F mediated by NO induces the activation of sGC and support the therapeutic strategy based on nitric oxide for patients with sickle-cell disease.

Furthermore, NO has vasodilator effects, which aggregates beneficial effects in physiopathology and in the treatment of sickle-cell disease. (KING, S. B. Free Rad. Biol. Med. v. 37, n 6, pp. 737-744, 2004).

The present invention relates to the novel use of some phthalimide derivatives and sulphonamide derivatives in the preparation of alternative drugs for the treatment of diseases which involve the need of reducing the levels of the TNF-α factor and the need of an exogenous source of nitric oxide. The invention described herein discloses a solution for the major limitations associated with the drug therapy of diseases which involve the need of reducing the levels of the TNF-α factor and the need of an exogenous source of nitric oxide, providing an alternative for the reduction of side and adverse effects of commonly-used compounds.

This invention also provides two new phthalimide derivatives which are used in the preparation of drugs for the treatment of said diseases, as well as a new process for obtaining a specific sulphonamide derivative also used in the preparation of drugs for the treatment of diseases which involve the need of reducing the levels of the TNF-α factor and the need of an exogenous source of nitric oxide. In a more particular aspect, the present invention overcomes the problems related with the major limitations and complications associated with the drug therapy conventionally used for the treatment of sickle-cell disease, thus improving the quality of life of the patient with sickle-cell disease.

BRIEF DESCRIPTION OF THE INVENTION

The present invention provides alternatives for the treatment of diseases in which there is an involvement of the increase of the TNF-α levels and the need of an exogenous source of nitric oxide for treatment.

In an aspect of the invention, the major limitations and complications associated with the drug therapy usually employed in the treatment of sickle-cell disease could be overcome or minimized with the use of the nitric oxide donor and TNF-α modulatory phthalimide and sulphonamide derivatives, thus improving the quality of life of the patient with sickle-cell disease.

The present invention refers to the use of a compound of general formula (I)

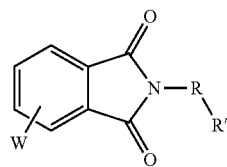

(I)

wherein W=H, halogen, $NO_2$, $NH_2$, OH, $C_1$-$C_6$ alcoxy, $C_1$-$C_6$ haloalcoxy, $C_1$-$C_6$ haloalkyl; R corresponds to $C_1$-$C_7$ alkyl, 2-phenyl, 3-phenyl, 4-phenyl, 2-benzyl, 3-benzyl, 4-benzyl, 2-ethylbenzyl, 3-ethylbenzyl, 4-ethylbenzyl, benzyl, thiophene, furan, pyrrole, 2-pyridine, 3-pyridine, 4-pyridine, pyrazine, pyrimidine, benzothiophene, benzofuran, indole, quinoline, isoquinoline, naphthalene, $CH_2$-2-thiophene, $CH_2$-3-thiophene, $CH_2$-2-furan, $CH_2$-3-furan, $CH_3CH_2$-2-thiophene, $CH_3CH_2$-3-thiophene, $CH_3CH_2$-2-furan, $CH_3CH_2$-3-furan; R' corresponds to O—$NO_2^-$ or $SO_2NHOH$ or furoxan; or any pharmaceutically acceptable salt thereof, in the preparation of a drug for the treatment of diseases which require reducing the levels of the TNF-α factor and an exogenous source of nitric oxide.

The invention also refers to the use of a compound of general formula (II)

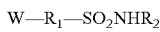  W—$R_1$—$SO_2NHR_2$ (II)

wherein W=H, halogen, $NO_2$, $NH_2$, OH, $C_1$-$C_6$ alcoxy, $C_1$-$C_6$ haloalcoxy, $C_1$-$C_6$ haloalkyl, $R_1$ corresponds to 2-phenyl, 3-phenyl, 4-phenyl, 2-benzyl, 3-benzyl, 4-benzyl, 2-ethylbenzyl, 3-ethylbenzyl, 4-ethylbenzyl, benzyl, thiophene, furan, pyrrole, 2-pyridine, 3-pyridine, 4-pyridine, pyrazine, pyrimidine, benzothiophene, benzofuran, indole, quinoline, isoquinoline, naphthalene, $CH_2$-2-thiophene, $CH_2$-3-thiophene, $CH_2$-2-furan, $CH_2$-3-furan, $CH_3CH_2$-2-thiophene, $CH_3CH_2$-3-thiophene, $CH_3CH_2$-2-furan, $CH_3CH_2$-3-furan; $R_2$ corresponds to OH, H, C(=O)NHOH, C(=S)NHOH, C(=O)NOH($C_6H_5$); or any pharmaceutically acceptable salt thereof, in the preparation of a drug for the treatment of diseases which require reducing the levels of the TNF-α factor and an exogenous source of nitric oxide.

The invention still refers to a pharmaceutical composition for the treatment of diseases which require reducing the levels of the TNF-α factor and an exogenous source of nitric oxide comprising said composition, said compound being selected among those resulting from formulae I and/or II or combinations thereof in a pharmaceutically acceptable carrier.

The invention also refers to a method for obtaining the compound of formula IIA

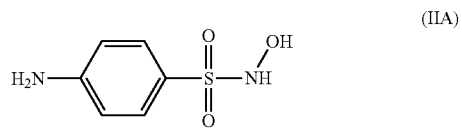

(IIA)

comprising the following steps of:
a) mixing, in a suitable container, hydroxylamine hydrochloride, sodium bicarbonate and water
b) adding ethanol to the mixture obtained in step a
c) adding 4-(1,3-dioxo-1,3-dihydro-2H-isoindol-2-yl) benzenesulphonyl chloride to the mixture obtained in step b The invention still refers to a compound of formula (IC):

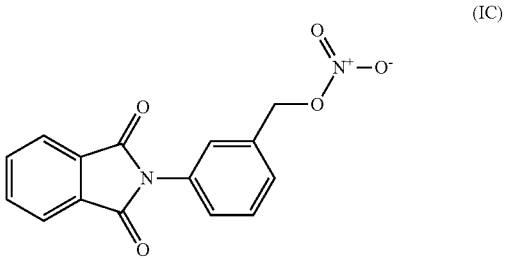

(IC)

and also to a compound of formula (IE)

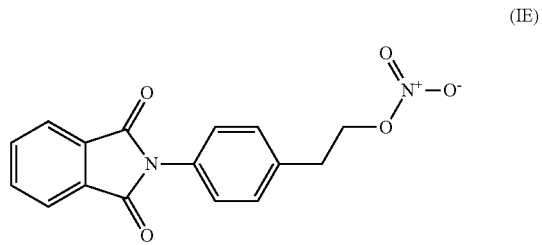

(IE)

DETAILED DESCRIPTION OF THE INVENTION

Figure 1:
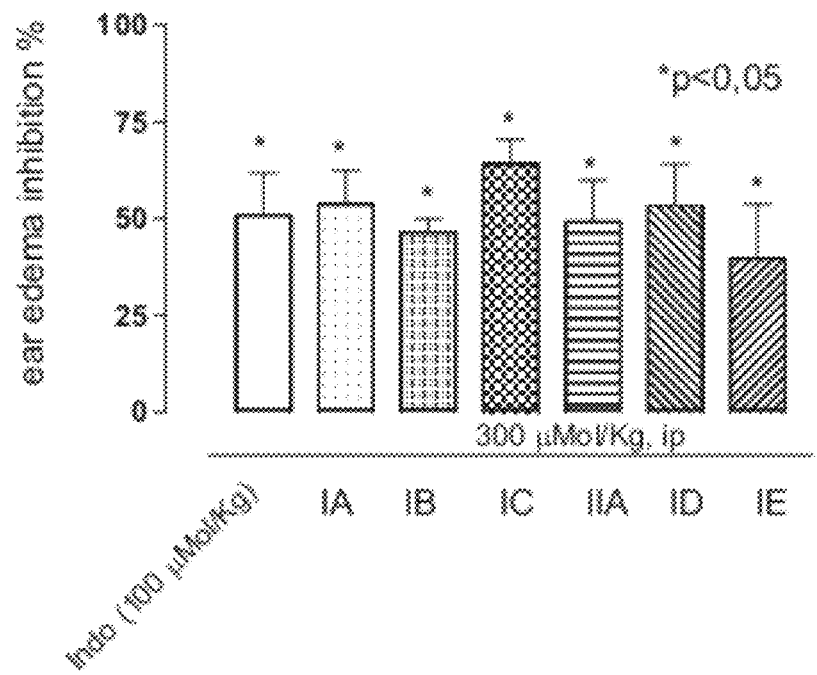
FIG. 1—Effect of derivatives (300 μmol/Kg), via i.p, in a mouse ear edema assay induced by capsaicin. Values represent the mean and standard error of the average of 5 animals. (*p<0.05 was considered significant at the 95% confidence level using Student's t test)

Currently, there is no specific treatment for hematologic diseases of genetic origin, but there are on the market drugs which are useful to the symptomatic treatment, which improve the quality of life of patients bearing these diseases.

The present invention has as its main novel characteristic the use of functionalized phthalimide and/or sulphonamide derivatives in the preparation of drugs for the treatment of diseases which require reduced levels of the TNF-α factor and an exogenous source of nitric oxide. The invention also has as a novel characteristic the disclosure of new functionalized phthalimide derivatives designed from the prototypes thalidomide and hydroxyurea, and designed rationally through the strategy of molecular hybridization for the treatment of said diseases. The invention also comprises, as another novel characteristic, a new method for obtaining a specific sulphonamide derivative which can be used in the preparation of a drug for the treatment of diseases which require reducing the levels of the TNF-α factor and an exogenous source of nitric oxide.

The new derivative was obtained with good to excellent chemical yields, by employing a methodology characterized by having a few synthetic steps, from commercially-available compounds, which qualifies this methodology for industrial use.

The present invention refers to the use of a compound of general formula (I)

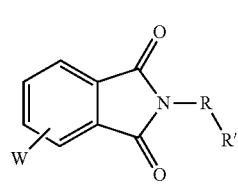

(I)

wherein W=H, halogen, $NO_2$, $NH_2$, OH, $C_1$-$C_6$ alcoxy, $C_1$-$C_6$ haloalcoxy, $C_1$-$C_6$ haloalkyl; R corresponds to $C_1$-$C_7$ alkyl, 2-phenyl, 3-phenyl, 4-phenyl, 2-benzyl, 3-benzyl, 4-benzyl, 2-ethylbenzyl, 3-ethylbenzyl, 4-ethylbenzyl, benzyl, thiophene, furan, pyrrole, 2-pyridine, 3-pyridine, 4-pyridine, pyrazine, pyrimidine, benzothiophene, benzofuran, indole, quinoline, isoquinoline, naphthalene, $CH_2$-2-thiophene, $CH_2$-3-thiophene, $CH_2$-2-furan, $CH_2$-3-furan, $CH_3CH_2$-2-thiophene, $CH_3CH_2$-3-thiophene, $CH_3CH_2$-2-furan, $CH_3CH_2$-3-furan; R" corresponds to O—$NO_2^-$ or $SO_2NHOH$ or furoxan; or any pharmaceutically-acceptable salt thereof, in the preparation of a drug for the treatment of diseases which require reducing the levels of the TNF-α factor and an exogenous source of nitric oxide. Preferably, the compound of general formula I described is used in the preparation of a drug for the treatment of sickle-cell disease.

In a preferred embodiment of the invention, the compound designated by (1,3-dioxo-1,3-dihydro-2H-isoindol-2-yl)methyl nitrate is used in the preparation of a drug for the treatment of diseases which require reducing the levels of the TNF-α factor and an exogenous source of nitric oxide. Said compound has the structural formula (IA):

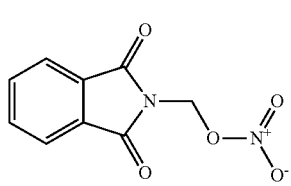

(IA)

and is preferably used in the preparation of a drug for the treatment of sickle-cell disease.

In another preferred embodiment of the invention, the compound designated by 2-(1,3-dioxo-1,3-dihydro-2H-isoindol-2-yl)ethyl nitrate is used in the preparation of a drug for the treatment of diseases which require reducing the levels of the TNF-α factor and an exogenous source of nitric oxide. Said compound has the structural formula shown as follows (IB):

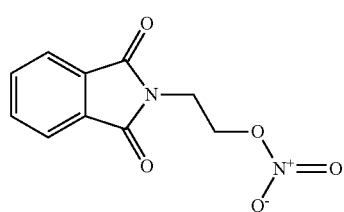

(IB)

and is preferably used in the preparation of a drug for the treatment of sickle-cell disease.

Another preferred embodiment of the invention uses the compound designated by 3-(1,3-dioxo-1,3-dihydro-2H-isoindol-2-yl)benzyl nitrate in the preparation of a drug for the treatment of diseases which require reducing the levels of the TNF-α factor and an exogenous source of nitric oxide. Said compound has the structural formula (IC):

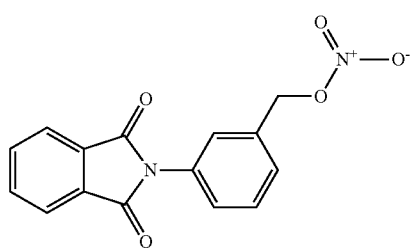

(IC)

and is preferably used in the preparation of a drug for the treatment of sickle-cell disease.

In still another preferred embodiment of the invention, the compound designated by 4-(1,3-dioxo-1,3-dihydro-2H-isoindol-2-yl)benzyl nitrate is used in the preparation of a drug for the treatment of diseases which require reducing the levels of the TNF-α factor and an exogenous source of nitric oxide. Said compound has the structural formula (ID):

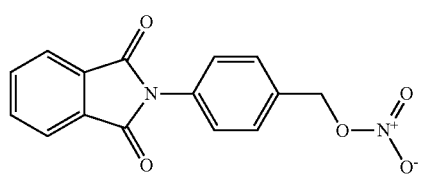

(ID)

and is preferably used in the preparation of a drug for the treatment of sickle-cell disease.

In another preferred embodiment of the invention, the compound designated by 2-[4-(1,3-dioxo-1,3-dihydro-2H-isoindol-2-yl)phenyl]ethyl nitrate is used in the preparation of a drug for the treatment of diseases which require reducing the levels of the TNF-α factor and an exogenous source of nitric oxide. Said compound has the structural formula (IE):

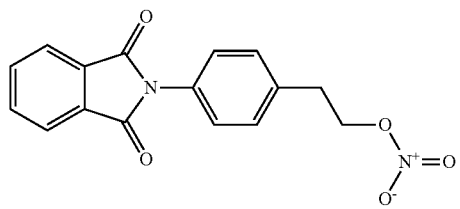

(IE)

and is preferably used in the preparation of a drug for the treatment of sickle-cell disease.

The present invention also refers to the use of a compound of general formula (II)

$$W-R_1-SO_2NHR_2 \quad (II)$$

wherein W=H, halogen, $NO_2$, $NH_2$, OH, $C_1$-$C_6$ alcoxy, $C_1$-$C_6$ haloalcoxy, $C_1$-$C_6$ haloalkyl, $R_1$ corresponds to 2-phenyl, 3-phenyl, 4-phenyl, 2-benzyl, 3-benzyl, 4-benzyl, 2-ethylbenzyl, 3-ethylbenzyl, 4-ethylbenzyl, benzyl, thiophene, furan, pyrrole, 2-pyridine, 3-pyridine, 4-pyridine, pyrazine, pyrimidine, benzothiophene, benzofuran, indole, quinoline, isoquinoline, naphthalene, $CH_2$-2-thiophene, $CH_2$-3-thiophene, $CH_2$-2-furan, $CH_2$-3-furan, $CH_3CH_2$-2-thiophene, $CH_3CH_2$-3-thiophene, $CH_3CH_2$-2-furan, $CH_3CH_2$-3-furan; $R_2$ corresponds to OH, H, C(=O)NHOH, C(=S)NHOH, C(=O)NOH($C_6H_5$); or any pharmaceutically-acceptable salt thereof, in the preparation of a drug for the treatment of diseases which require reducing the levels of the TNF-α factor and an exogenous source of nitric oxide. Preferably, the compound of general formula previously described is used in the preparation of a drug for the treatment of sickle-cell disease.

In a preferred embodiment of the invention, the compound designated by 4-amino-N-hydroxybenzenesulphonamide is used in the preparation of a drug for the treatment of diseases which require reducing the levels of the TNF-α factor and an exogenous source of nitric oxide. Said compound has the structural formula (IIA):

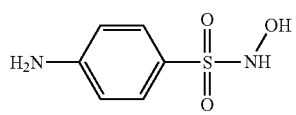

(IIA)

and is preferably used in the preparation of a drug for the treatment of sickle-cell disease.

The subject invention still refers to pharmaceutical compositions for the treatment of diseases which require reducing levels of the TNF-α factor and an exogenous source of nitric oxide comprising said compositions, said compounds being selected among those resulting from formulae I and/or II or combinations thereof. The compositions described in the subject invention comprise compounds of general formula I and/or II or pharmaceutically acceptable salts thereof, in association with a pharmaceutically acceptable excipient.

The pharmaceutical compositions of the present invention may be administered in a variety of dosage forms, such as orally, in the form of tablets, capsules, sugar or tablets covered with a film, liquid solutions or suspensions; rectally in the form of suppositories; parenterally, i.e., intramuscularly, or by infusion or intravenous and/or intrathecal and/or intraspinal injection.

The pharmaceutical compositions to which this invention relates are usually prepared according to conventional methods and administered in a suitable pharmaceutical form.

Solid oral pharmaceutical forms may contain, together with the active compound, different diluents, such as lactose, dextrose, saccharose, cellulose, corn starch, potato starch, or other suitable diluents; lubricants, such as silica, talc, stearic acid, magnesium or calcium stearate, and/or polyethylene glycols or other pharmaceutically acceptable lubricants; binding agents such as starches, gum arabic, gelatin, methylcellulose, carboxymethylcellulose, polyvinylpyrrolidone, or other suitable binding agents; disaggregating agents, such as starch, alginic acid, alginates or starch or sodium glycolate, or other suitable disaggregating agents; effervescent mixtures; dyes; sugary materials; wetting agents such as lectin, polysorbates, laurylsulphates; and, generally, non-toxic pharmacologically inactive substances used in pharmaceutical formulations. Preparations of said pharmaceutical compositions may be performed in a known way, such as by means of mixture, granulation, pressing into tablets, sugar covering, film coating processes or other suitable processes.

Liquid dispersions for oral administration may include, for example, syrups, emulsions and suspensions. Syrups may contain, as a carrier, for example, saccharose or saccharose with glycerine and/or mannitol and/or sorbitol or another pharmaceutically acceptable carrier. Suspensions and emulsions may contain, as a carrier, among others, a natural gum, agar, sodium alginate, pectin, methylcellulose, carboxymethylcellulose, polyvinyl alcohol or other suitable carriers.

Suspensions or solutions for intramuscular injection may contain, together with the active compound, a pharmaceutically acceptable carrier, i.e., sterile water, olive oil, ethyl oleate, glycols, i.e., polyethylene glycol, or other pharmaceutically acceptable carrier, and, if desired, a suitable amount of lidocaine hydrochloride. Solutions for intravenous injections or infusions may contain, as a carrier, for example, sterile water, or preferably, they may be in the form of sterile salt, aqueous or isotonic solutions, or may contain, as a carrier, propylene glycol or another pharmaceutically acceptable carrier.

The suppositories may contain, together with the active compound, a pharmaceutically acceptable carrier, such as cocoa butter, polyethylene glycol, sorbitan polyoxyethylene, fatty acid ester surfactant, lecithin, or other pharmaceutically suitable carriers.

The present invention also refers to a novel method for obtaining the compound designated by 4-amino-N-hydroxybenzenesulphonamide of formula (IIA)

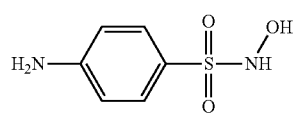

(IIA)

through the following steps of:
a) mixing, in a suitable container, hydroxylamine hydrochloride, sodium bicarbonate and water
b) adding ethanol to the mixture obtained in step a
c) adding 4-(1,3-dioxo-1,3-dihydro-2H-isoindol-2-yl) benzenesulphonyl chloride to the mixture obtained in step b In a preferred embodiment of the invention, the synthesis of 4-amino-N-hydroxybenzenesulphonamide is carried out by adding, into a 10 mL round-bottom flask, 21.6 mg of hydroxylamine hydrochloride (0.31 mmol), 26.1 mg of sodium bicarbonate (0.31 mmol), and 0.1 ml of distilled water. Upon ceasing the elimination of $CO_2$, 2 mL of ethanol was added. Next, 100 mg of 4-(1,3-dioxo-1,3-dihydro-2H-isoindol-2-yl)benzenesulphonyl chloride (0.31 mmol) were added. The reaction was observed by thin layer chromatography (TLC) (eluent: 100% Dichloromethane) until the end of reaction was indicated. After 45 minutes under reaction, the solvent is evaporated under reduced pressure, and the obtained product is washed with hot dichloromethane (so as not to remove the 4-(1,3-dioxo-1,3-dihydro-2H-isoindol-2-yl)benzenesulphonyl chloride which did not react in order to give approximately 82 mg (80%) of 4-amino-N-hydroxybenzenesulphonamide as a white powder, with a melting range higher than 275° C. ($C_{14}H_8ClNO_4S$; PM=318.306). The compound obtained (4-amino-N-hydroxybenzenesulphonamide) through the described method is used, as detailed previously, in the treatment of diseases which require reducing the levels of the TNF-α factor and an exogenous source of nitric oxide. Preferably, the obtained compound (4-amino-N-hydroxybenzenesulphonamide) is used in the preparation of a drug for the treatment of sickle-cell disease.

The present invention still refers to a new phthalimide derivative designated by 3-(1-3-dioxo-1,3-dihydro-2H-isoindol-2-yl)benzyl nitrate represented by the formula shown as follows (IC)

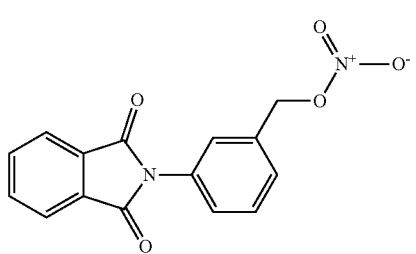

(IC)

and used, as described previously, in the preparation of a drug for the treatment of diseases which require reducing the TNF-α levels and an exogenous source of nitric oxide.

The invention also refers to another phthalimide derivative designated by 2-[4-(1-3-dioxo-1,3-dihydro-2H-isoindol-2-yl)phenyl]ethyl nitrate of general formula shown as follows (IE)

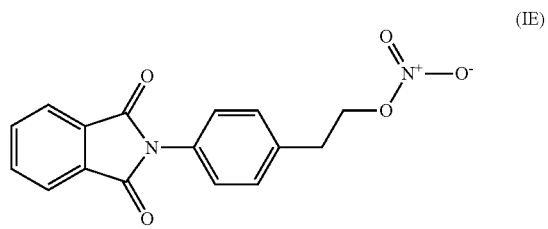

(IE)

and used, as described previously, in the preparation of a drug for the treatment of diseases which require reducing the TNF-α levels and an exogenous source of nitric oxide.

The compounds described in the present invention were subjected to a number of tests in order to ensure the intended activities in the treatment of diseases which require reducing the TNF-α levels and an exogenous source of nitric oxide. Particularly, the compounds were subjected to tests in order to ensure their activity as auxiliary agents in the treatment of symptoms of sickle-cell disease. The tests carried out and the results obtained are described in the following.

Mutagenic Activity Test

Firstly, the compounds were evaluated with the AMES test in order to identify a possible mutagenicity. This test is important to obtain compounds having a lower genotoxic profile, and also guides molecular changes to obtain more safe compounds. The tests were conducted with the previously described compounds of general formula IA, IB, IC, ID, IE, and IIA and are shown in tables 1, 2 and 3 below.

TABLE 1

Mutagenic evaluation in *Salmonella typhimurium* TA100 and TA102 strains in the presence and absence of metabolic activation (S9) of the compound IA.

| Compound | concentration nmol/plate | TA 100 +S9 | TA 100 −S9 | TA 102 +S9 | TA 102 −S9 |
|---|---|---|---|---|---|
| IA | 0 | 129.3 ± 8.1 | 136.7 ± 12.4 | 213.5 ± 15.5 | 197.33 ± 16.01 |
|  | 7.25 | 154 ± 14.2 (1.19) | 140.5 ± 17 (1.03) | 298 ± 11.3 (1.4) | 263.7 ± 15 (1.33) |
|  | 14.5 | 155 ± 5.9 (1.19) | 161.7 ± 11 (1.18) | 320.8 ± 17 (1.5) | 249.7 ± 12 (1.26) |
|  | 29 | 140.3 ± 2 (1.08) | 122.7 ± 3.06 (0.9) | 385 ± 21.8 (1.8) | 261.3 ± 20 (1.32) |
|  | 56 | 126.3 ± 8.1 (0.97) | 234 ± 39.5 (1.71) | 499 ± 8.9 (2.34) | 153 ± 21 (0.77)* |
|  | 112 | 133.3 ± 11 (1.03) | 335 ± 15.7 (2.45) | 351.2 ± 12 (1.64)* | 141 ± 18 (0.71)* |

*cell death

TABLE 2

Mutagenic evaluation in *Salmonella typhimurium* TA100 and TA102 strains in the presence and absence of metabolic activation (S9) of compounds IB, IC and IIA.

| COMPOUND | concentration μmol/plate | TA 100 +S9 | TA 100 −S9 | TA 102 +S9 | TA 102 −S9 |
|---|---|---|---|---|---|
| IB | 0 | 104 ± 7.4 | 115 ± 13.2 | 219 ± 8.9 | 323 ± 10.2 |
|  | 0.01 | 354 ± 6.9 (3.4) | 171 ± 48.9 (1.49) | 249 ± 11.7 (1.13) | 394 ± 30 (1.22) |

TABLE 2-continued

Mutagenic evaluation in *Salmonella typhimurium* TA100 and TA102 strains in the presence and absence of metabolic activation (S9) of compounds IB, IC and IIA.

| COMPOUND | concentration μmol/plate | TA 100 +S9 | TA 100 −S9 | TA 102 +S9 | TA 102 −S9 |
|---|---|---|---|---|---|
|  | 0.021 | 335 ± 10.8 (3.22) | 200 ± 23.3 (1.74) | 269 ± 10.6 (1.22) | 452 ± 23 (1.55) |
|  | 0.042 | 397 ± 25.9 (3.8) | 223 ± 45.04 (1.94) | 239 ± 22.5 (1.09) | 502 ± 14 (1.25) |
|  | 0.085 | 395 ± 40.2 (3.8) | 206 ± 30.2 (1.8) | 247 ± 21.4 (1.12) | 405 ± 24 (1.34) |
|  | 0.17 | 261 ± 11 (2.5)* | 165 ± 11.1 (1.43)* | 214 ± 32 (0.97)* | 433 ± 35.4 (1.54) |
| IC | 0 | 129 ± 8.1 | 179 ± 8.72 | 372 ± 27.5 | 254.7 ± 14.6 |
|  | 0.224 | 165 ± 13.2 (1.27) | 216.7 ± 10.2 (1.21) | 272 ± 26 (0.73) | 281 ± 25 (1.10) |
|  | 0.488 | 153 ± 13.1 (1.18) | 224.5 ± 24.6 (1.25) | 378 ± 6.1 (1.01) | 286 ± 4.2 (1.12) |
|  | 0.896 | 146 ± 5 (1.12) | 266.3 ± 8.4 (1.48) | 405 ± 11 (1.09) | 303 ± 9.2 (1.19) |
|  | 1.8 | 163 ± 22.5 (1.26) | 239.7 ± 11.3 (1.34) | 399.3 ± 40 (1.07) | 395.7 ± 9 (1.55) |
|  | 3.58 | 158.3 ± 9.3 (1.22) | 323.7 ± 10.2 (1.8) | 431 ± 17.9 (1.15) | 387 ± 9.7 (1.52) |
| IIA | 0 | 129.3 ± 8.14 | 146.7 ± 12.1 | 372.3 ± 27.5 | 197.3 ± 16.1 |
|  | 0.98 | 160 ± 12.4 (1.24) | 146.3 ± 5.1 (0.99) | 385 ± 33.1 (1.03) | 222 ± 12 (1.12) |
|  | 1.96 | 175.7 ± 2 (1.36) | 180.5 ± 7.8 (1.23) | 323 ± 5.54 (0.87) | 241 ± 13 (1.22) |
|  | 3.92 | 185.3 ± 15 (1.43) | 179 ± 11.3 (1.22) | 423.7 ± 22 (1.13) | 251 ± 19.2 (1.27) |
|  | 7.85 | 206 ± 13.6 (1.59) | 172.7 ± 12.5 (1.17) | 387 ± 14.4 (1.03) | 232 ± 13.1 (1.17) |
|  | 15.7 | 354 ± 6.5 (2.74) | 175 ± 2.8 (1.19) | 300 ± 4.9 (0.8)* | 210 ± 23 (1.06) |

*cell death

TABLE 3

Mutagenic evaluation in *Salmonella typhimurium* TA100 and TA102 strains in the presence and absence of metabolic activation (S9) of compounds ID and IE.

| COMPOUND | concentration μol/plate | TA 100 +S9 | TA 100 −S9 | TA 102 +S9 | TA 102 −S9 |
|---|---|---|---|---|---|
| ID | 0 | 129.3 ± 8.1 | 179 ± 8.7 | 372.3 ± 27.5 | 260.1 ± 11.6 |
|  | 0.224 | 157 ± 13 (1.21) | 228 ± 18 (1.27) | 405.7 ± 13 (1.09) | 340.3 ± 9.7 (1.31) |
|  | 0.488 | 184.7 ± 16 (1.42) | 239 ± 11.5 (1.33) | 434.7 ± 21 (1.16) | 373.5 ± 21 (1.43) |
|  | 0.896 | 216.7 ± 18 (1.67) | 231 ± 20.2 (1.29) | 370 ± 6 (0.99) | 391.2 ± 6.3 (1.5) |
|  | 1.8 | 192.7 ± 16 (1.49) | 212.3 ± 17 (1.18) | 397.3 ± 9.3 (1.06) | 486.8 ± 20 (1.87) |
|  | 3.58 | 263 ± 12.3 (2.03) | 349 ± 5.6 (1.94) | 427.3 ± 5 (1.14) | 420 ± 8.6 (1.62)* |
| IE | 0 | 129.3 ± 8.1 | 136.7 ± 12.4 | 372.3 ± 27.5 | 197.3 ± 16.1 |
|  | 0.12 | 363 ± 25.2 (2.8) | 143.3 ± 5 (1.04) | 335.3 ± 11 (0.9) | 256 ± 6.9 (1.29) |
|  | 0.25 | 478.7 ± 4.22 (3.7) | 135.3 ± 12 (0.99) | 295.3 ± 28 (0.8) | 262 ± 19.1 (1.32) |
|  | 0.5 | 628 ± 40.8 (4.86) | 136.3 ± 13 (0.99) | 406 ± 14.1 (1.09) | 266.7 ± 18 (1.35) |
|  | 1 | 739 ± 25.4 (5.72) | 121.5 ± 14 (0.89) | 465 ± 10.6 (1.25) | 265.7 ± 10 (1.34) |
|  | 2 | 750 ± 13.6 (5.79) | 177 ± 23.6 (1.30) | 447 ± 19.8 (1.2) | 201 ± 4.7 (1.02)* |

*morte celular

The compound of formula IA showed mutagenicity ratios (RM) of 2.45 and 2.34; in the TA100 strain, the absence of metabolic activation (112 nmol/plate), and in the TA102 strain, in the presence of metabolic activation (56 nmol/plate), respectively. At concentrations higher than 56 nmol in TA102 (+S9), toxicity can be observed, with a reduction on the number of revertants per plate (Table 01). Compound IA is an alkyl derivative which has reactive methylene carbon, i.e., the carbon atom has a positive partial charge by removal of the electron density due to the more electronegative a moieties. The presence of this methylene carbon promotes the attack by bionucleophiles, leading to elimination of the nitrate, which readily decomposes into a radical species generating a number of detrimental effects in the DNA of the prokaryote, which does not have a repair system as efficient as that of eukaryotes. Further, there may occur addition of the bionucleophile into the reactive methylene carbon, resulting in the formation of a covalent adduct, irreversibly modifying the original structure of said bionucleophile.

The compound of formula IB shows, at the concentrations used, mutagenicity in TA100 strain in the presence of metabolic activation, at all tested concentrations and with the following mutagenicity ratios (MR): 0.01 µmol (3.4); 0.021 µmol (3.22); 0.042 µmol (3.8); 0.085 µmol (3.8) e 0.17 µmol (2.5) (Table 02). Among the alkyl series tested, that was the one which showed the highest MR. When compound IB is compared with compound IA, it can be clearly seen that the latter has a lower hindrance to attacks on the methylene carbon, facilitating the access of the bionucleophile. The hindrance in compound IA is higher due to the presence of bulky moieties at positions a. This could account for the higher mutagenicity ratio of compound IB, and allows us to predict that methylene compounds will be less mutagenic than ethylene compounds. This hypothesis is better analyzed through the results of tests with compounds ID and IE.

Compound IC did not show mutagenicity at the concentrations used, although in the test with the TA100 strain in the absence of metabolic activation and at the concentration of 3.58 µmol/plate, it showed a mutagenicity ratio of 1.8; that is, signs of mutagenicity (Table 01). When compound IA is compared with compound IC, it can be observed that the latter—an interphenylene derivative—has a lower mutagenicity since the sign has appeared only at 3.58 µmol/plate, while in compound IA, mutagenicity has occurred at 112 nmol/plate with a MR of 2.45 (TA100; –S9). Also, when the compound IC is compared with the compound IB, it can be observed a lower mutagenicity of the interphenylene derivative. These data suggest that the aryl derivatives, that is, those having an aromatic ring bonded to the phthalimide moiety (compounds IC, ID, IE and IIA), have a lower mutagenicity than the alkyl derivatives, that is, those in which the alkyl chain is directly bonded to the phthalimide moiety (compounds IA and IB); supporting the hypothesis that steric factors hinder the access of the bionucleophile to the reactive site, modulating the mutagenicity of the synthesized derivatives.

The compound IIA is a sulphonamide derivative which does not have the nitrate moiety, common to all other compounds. The literature reports that hydroxylamine derivatives, or hydroxamic acid derivatives, show mutagenicity largely due to the major toxicophoric contribution from this moiety (ZHU, X. et al. Mut. Res. v. 425, pp. 153-167, 1999). For a long time, the hydroxylamine moiety has been pointed out as one of the main metabolites, generated in the reduction of the nitro group, responsible for the mutagenic activity of nitro compounds (e.g., chloramphenicol, metronidazole, and nitrofurans). Nevertheless, it has been found that they are radical species formed in steps prior to reductions which generate mutagenic products rather than the hydroxylamine derivative itself (TOCHER, J. H. Gen. Pharmac. v. 28, n. 4. pp. 485-487, 1997).

Thus, the compound IIA containing the hydroxylamine moiety was evaluated in order to verify the toxicophoric contribution from this moiety in the synthesized compound. This derivative was subsequently reacted with phthalic anhydride to obtain a phthalimide derivative.

At the concentration of 15.7 µmol/plate in the TA100 strain, with metabolic activation, the compound IIA exhibited a mutagenicity ratio of 2.74. Above 15.7 µmol/plate, there is a reduction on the number of revertants per cell toxicity. The possible mutagenesis of compound IIA, which occurs only in the presence of metabolic activation, could be assigned to the formation of a radical and/or oxidized derivative from this compound. When comparing the concentration of compound IIA used in the test with the aryl derivatives (compounds IC, ID and IE), it can be seen that, although there is mutagenesis, it is observed only at high concentrations, being up to 125 times higher, in number of moles, than that found for compound II (0.12 µmol/plate).

The compound ID showed in the TA100 strain, in the presence of metabolic activation and at a concentration of 3.58 µmol/plate, a mutagenicity ratio of 2.03; while in the absence of metabolic activity, at this same concentration, it showed mutagenicity signs with MR values of 1.94. At a concentration of 1.8 µmol/plate in the absence of S9, in the TA102 strain, it showed mutagenicity signs, with a MR of 1.87 (Table 03). When comparing the compound ID, a regioisomer of the compound IC, we observed a discrete profile of higher mutagenicity and/or a mutagenicity sign of the compound ID with respect to compound IC.

The compound IE, an interphenylene derivative of compound IB, in the TA100 strain and in the presence of metabolic activation, showed, as well as compound IB, mutagenesis at concentrations of 0.12; 0.25; 0.5; 1 and 2 µmol/plate, with MR values of 2.8; 3.7; 4.86; 5.72 e 5.79, respectively (Table 03). Although MR values are higher in compound II with respect to compound IB, the latter is at a lower molar concentration. The need for higher concentrations for compound II to show mutagenesis confirms, in structural terms, what had already been observed between compounds IA and IC: the presence of phenyl bonded to the phthalimide moiety reduces the mutagenicity of the compounds.

When comparing compound II with compound ID, both para-substituted, we could also confirm, as seen between compounds IA and IB, that the ethyl spacing increases mutagenesis, when compared to methyl spacing. As discussed previously, this factor is probably related, besides the electron factor, mainly to the steric factor, due to the better access by nucleophiles to the carbon a to the nitrate moiety.

When relating the obtained compounds with thalidomide and hydroxyurea patterns, we observed a sensitivity of the AMES test in responding to the examples, when compared to HU and thalidomide. This observation, although it suggests a higher mutagenic activity of the synthesized compounds regarding the patterns of structural planning, can not be conclusive, and more tests are required for such statement. In addition, thalidomide, HU and synthesized compounds are structurally distinct and, due to this chemical particularity, could show a differentiated mutagenic profile.

From the sets of results obtained in the AMES test, we could infer that:

Alkyl derivatives (compounds IA and IB) show higher mutagenicity expressed by the average of the number of revertants/plate than aryl derivatives (compounds IIA, IC and ID);

Derivatives with ethylene spacing show higher mutagenesis than methylene compounds;

This set of results allows us to conclude that the benzyl spacing is more suitable in order to obtain compounds with lower mutagenicity.

Further, even for mutagenic compounds, a mutagenicity ratio of 2 is considered low if compared to drugs used in therapeutics, such as metronidazole, which has a MR of 14.9 when tested at 58.4 µmol in TA 100 without metabolic activation (SILVA, A. T. A. et al. Mini Rev. Med. Chem., v. 5, pp. 893-914, 2005). This allows us to conclude that although there are signs of mutagenicity for the compounds, it is too low, and these results may not reflect in eukaryotic cells.

Mouse Ear Edema Assay Induced by Capsaicin

This assay is characterized by an acute inflammatory response of the ear, with development of edema, and it was performed in order to evaluate the anti-inflammatory activity of the synthesized compounds.

In this assay, indomethacin was used as a control at 100 μmol/Kg, and the phthalimide derivatives were firstly evaluated at 300 μmol/Kg via i.p. From table 4, it can be observed that compounds IC and IE show an ear edema inhibition percentage higher than 64%. Compound IC showed an inhibition percentage of about 64.09% in the performed assay. The other compounds, however, show a similar activity when compared to indomethacin (FIG. 01), taking into consideration the standard error. These results suggest that the synthesized compounds show anti-inflammatory activity in the acute phase, probably due to the inhibition of the cytokine TNFα, since it is known that phthalimide derivatives have this activity.

TABLE 4

Ear edema assay induced by capsaicin (i.p.)

| | + Control | Compound IA | Compound IB | Compound IC | Compound IIA | Compound ID | Compound IE |
|---|---|---|---|---|---|---|---|
| N | 5 | 5 | 5 | 5 | 5 | 5 | 5 |
| Average inhibition % | — | 53.75 | 46.55 | 64.09 | 49.24 | 37.18 | 76.58 |
| EPM | — | 8.66 | 3.49 | 6.44 | 10.58 | 19.38 | 5.32 |

\* Animals showed higher values than controls

Peritonitis Assay

Figure 2:
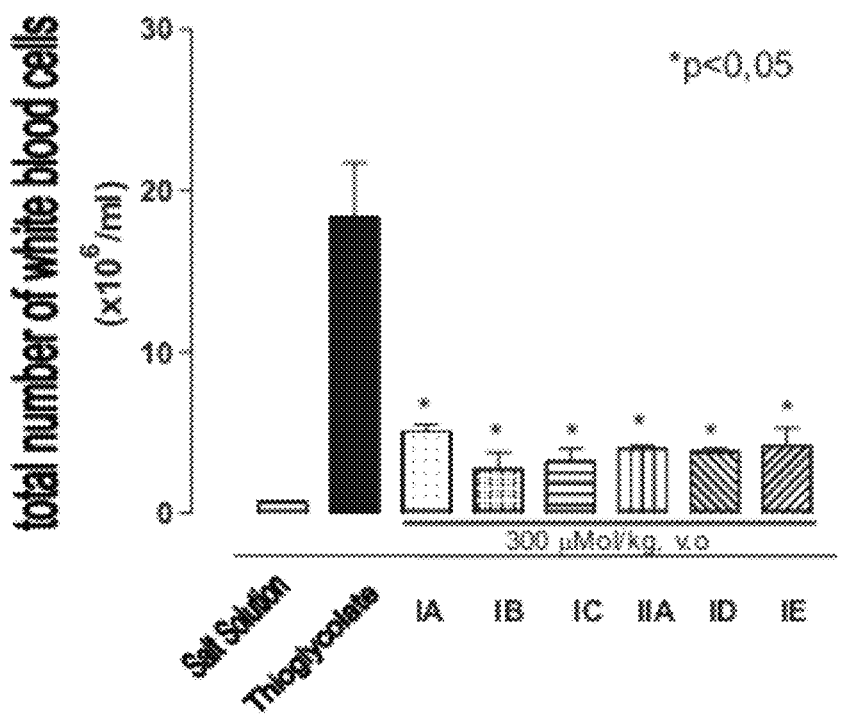
FIG. 2—Effect of derivatives (300 μMol/Kg), administered orally, in a peritonitis assay induced by 3% thioglycolate in mouse. Values represent the mean and standard error of the average of 4 animals. (*p<0.05 was considered significant at the 95% confidence level using Student's t test)

In a second assay, the number of total leukocytes ($10^6$/mL) was evaluated in order to evaluate the ability to inhibit their infiltration in the inflammatory process. All phthalimide derivatives showed inhibition activity of the leukocyte infiltrate (FIG. 2; Table 5) with a similar activity profile, considering the standard error. These results demonstrate the anti-inflammatory potential of these compounds.

TABLE 5

Results of the peritonitis assay

| | + Control | Compound IA | Compound IB | Compound IC | Compound IIA | Compound ID | Compound IE |
|---|---|---|---|---|---|---|---|
| N | 3 | 3 | 3 | 3 | 3 | 3 | 3 |
| Inhibition % | | 12.5 | 51.25* | 42.85 | 28.57 | 32.14 | 26.25 |
| Cell Number avg (×106) | 5.6 | 4.9 | 2.73 | 3.2 | 4.0 | 3.8 | 4.13 |
| EPM | 0.20 | 0.7 | 1.0 | 0.8 | 0.30 | 0.2 | 1.16 |

\# The animal has bleed
• P < 0.05 (Student's T test)

Abdominal Writhing Induced by Acetic Acid

In order to evaluate the peripheral analgesic activity of the compounds, an abdominal writhing assay induced by acetic acid (Table 6) was carried out. In this assay, we could infer that compound ID has an important analgesic activity, inhibiting abdominal writhing by 66%. Other compounds, such as IA, IIA and IE, also have significant inhibitions of the abdominal writhing induced by acetic acid, demonstrating the analgesic potential of these compounds. The analgesic activity may be related to the ability of these compounds to inhibit the cytokine TNFα, since it is known that this would be one of the mechanisms that explain the analgesia of molecules such as thalidomide.

TABLE 6

Abdominal writhing assay induced by acetic acid

| | + Control | Compound IA | Compound IB | Compound IIA | Compound ID | Compound IE |
|---|---|---|---|---|---|---|
| Average | 47.54 | 28.6 | 39.2 | 30.4 | 16.2 | |
| Inhibition % | — | 39.83 | 23.22 | 36.05 | 66.03 | 33.95 |
| EPM | 3.39 | 9.25 | 8.65 | 7.83 | 5.24 | 6.60 |

Assays for Evaluating the Increase of Gamma-Globin by PCR in K562 Cell Culture

Figure 3:
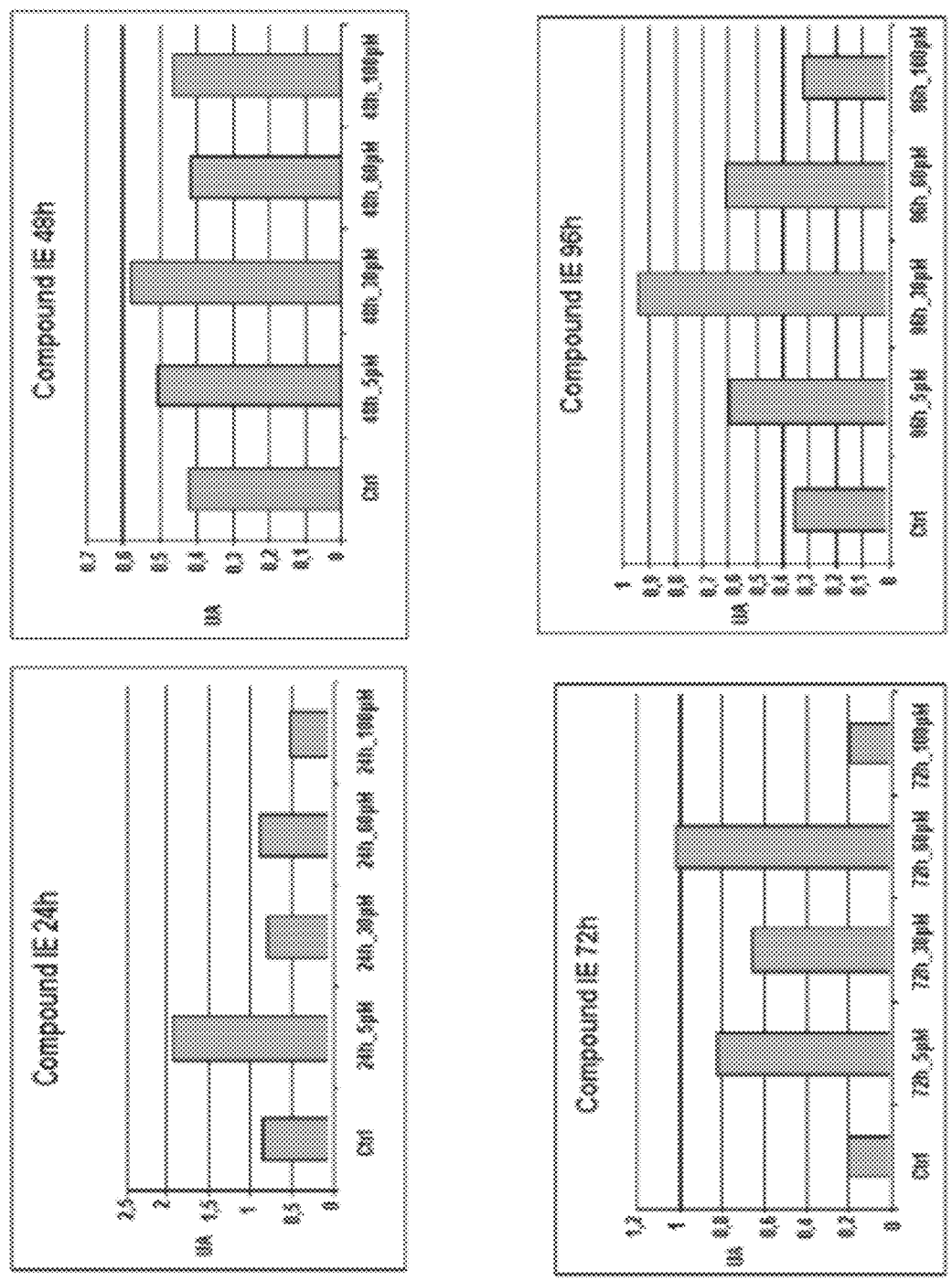
FIG. 3—Expression of gamma-globin mRNA in the presence of example 7 at different concentrations, in the absence of hemin, at times of 24 h, 48 h, 72 h and 96 h.
Figure 4:
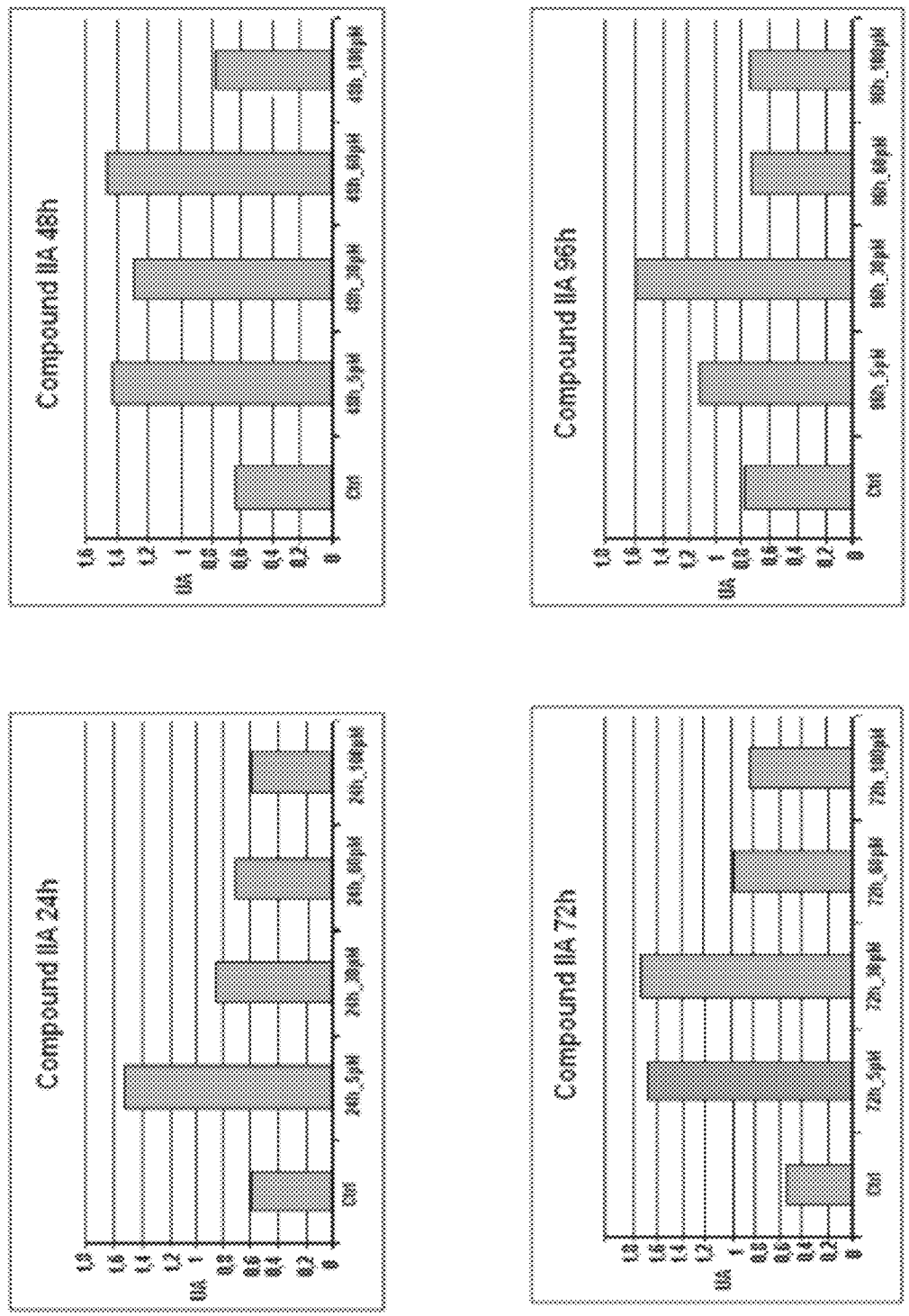
FIG. 4—Dose-response curve of compound IIA at concentrations of 5 μM, 30 μM, 60 μM and 100 μM at times 24 h, 48 h, 72 h and 96 h in the absence of hemin.

From results obtained in the evaluation of the gene expression induced by compounds in a culture of K562 erythroleukemic cells, and quantified by Real Time PCR, we can conclude that:

Compound II has activity in this model, increasing the gene expression of gamma-globin, in the presence or absence of hemin;

In the presence of hemin, compound II did not show a significantly higher activity than in the absence of hemin, when compared to the control (FIG. 3);

Apparently, compound II has an effect on the expression of gamma-globin at low concentration (5 µM e 30 µM);

The compound II showed high percentages of cell viability (higher than 90%) in assays with and without hemin, demonstrating the absence of toxic effects at the concentrations used;

Compound IIA showed higher activity than the control in the expression of gamma-globin (FIG. 4).

The increase on the expression of gamma-globin induced by compound IIA is higher than the increase provided by compound II, suggesting that compound IIA is more efficient in increasing the gene expression of gamma-globin.

When comparing the compound IIA with HU data in the literature, it was observed that the compound IIA shows activity at 5 µM in 48 hours, whereas for HU to produce a comparable activity, it is used at 10 µM in the same time.

Figure 5:
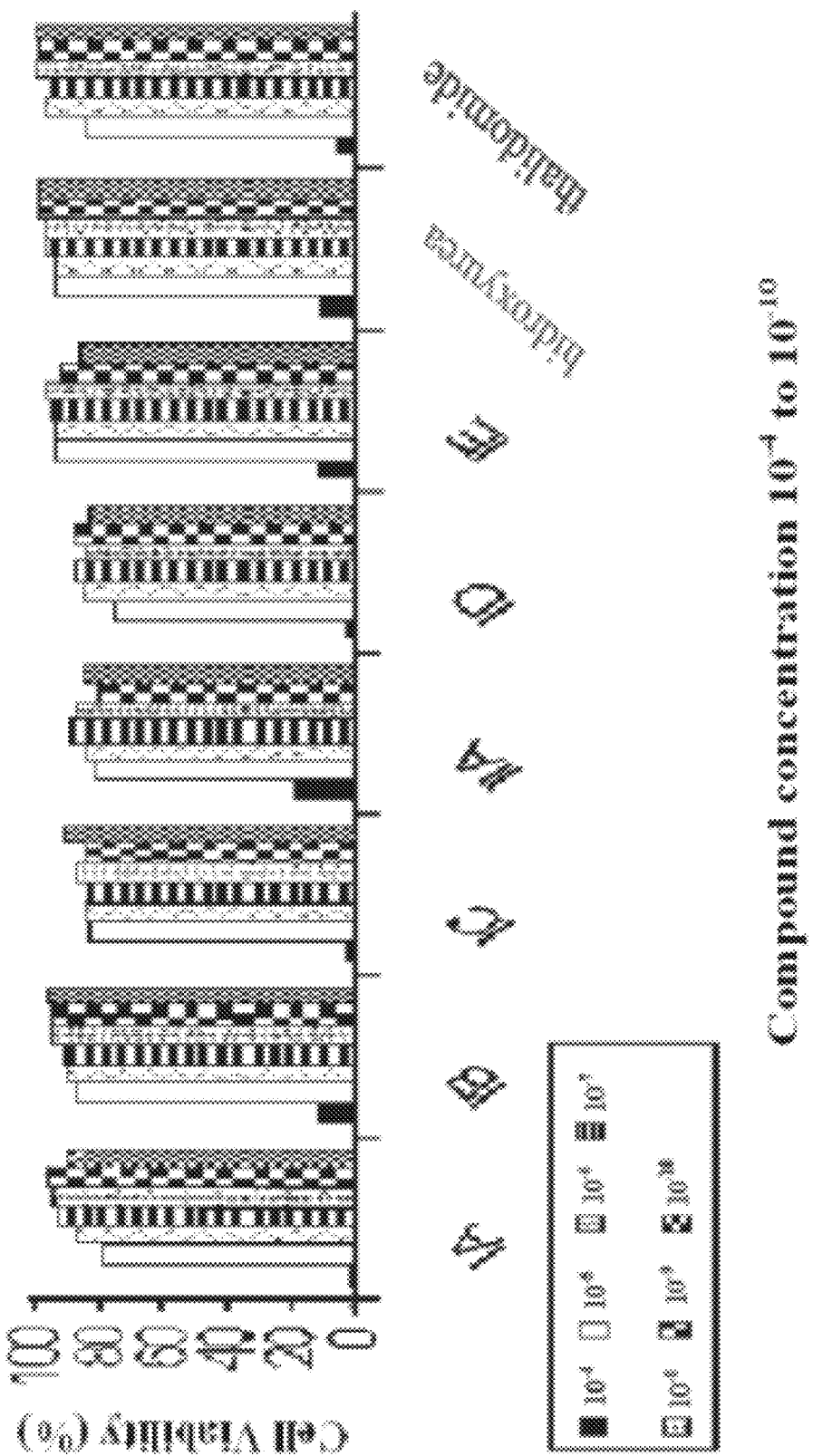
FIG. 5—Cell viability of the designed compounds.

The cell viability at 0 h was 97%, and this pattern was maintained during the realization of the assay, demonstrating the absence of toxicity of the compound IIA (FIG. 5).

Methodologies Used for Pharmacological Assays:

Procedures for Evaluating the Mutagenic Activity (AMES Test)

The procedure was firstly developed by (MARON, D. M. and AMES, B. N. Mut. Res. v. 113, pp. 173-215, 1983)

Strains Used in the Assay:

There are many genetically modified strains of *Salmonella typhimurium* in order to detect a prevalent type of mutation, which include: TA97, TA98, TA100 and TA102. TA100 and TA102 detect mutations which cause base pair substitutions, while TA 98 and TA 97 detect changes where there is a gap in the DNA reading frame (MARON & AMES, 1983).

For this assay, *Salmonella typhimurium* TA100 and TA102 strains from the mutagenicity laboratory of the "Faculdade de Ciências Farmacêuticas—UNESP Araraquara" were used. Such strains have the following characteristics: (AMES, 1983)

1—Are auxotrophic with respect to histidine;
2—Have various mutations in the histidine operon, which are target for reverse mutation;
3—Detect many mutagenic agents which cause shift in the DNA reading frame, which restore the correct reading frame for histidine synthesis;
4—Mutation in hisG46 gene, in the reading frame of the hisG gene, which encodes the first enzyme for histidine synthesis, TA 100-specific;
5—Mutation in gene hisD3052, constituted by 8 repeated residues of -GC-, near the shift mutation site in the reading frame of the hisD gene, which encodes the TA 98-specific histidinol dehydrogenase enzyme;
6—Mutation (rfa), which causes partial loss of the lipopolysaccharide barrier, increasing the permeability of the bacterial cell wall, facilitating the diffusion of large molecules into the cell;
7—Mutation (urvB), which causes damage in the repair system by excision, resulting in an increase on the detection sensitivity of various mutagenic agents. It also causes the bacterium to become dependant on biotin to grow;
8—Plasmid pKM101, which enhances the resistance to ampicillin, and also increases the spontaneous and chemical mutagenesis by stimulating the error-prone DNA repair system.

Maintenance and Storage of Strains

*Salmonella typhimurium* strains were stored in a freezer at −80° C., in flasks for freezing with 0.9 mL of culture and 0.1 mL of DMSO as a cryoprotector agent, so as to maintain all their genetic characteristics unchanged.

Before freezing, all strains had their genotypes confirmed (histidine auxotrophy, rfa mutation, pKM101 plasmid, uvrb deletion, and spontaneous reversion rate).

Preparation of Culture Media and Solutions

Vogel-Bonner Medium E (VB)

0.25 g of magnesium sulphate, 2.5 g of citric acid, 12.5 g of dibasic potassium phosphate, and 4.375 g of sodium and ammonium phosphate were dissolved into 16.75 mL of distilled water at 45° C. (amounts enough for 25 mL of VB solution). The solution was sterilized in an autoclave for 15 minutes at 121° C.

40% Glucose 50 mL of a 40% glucose solution were prepared, which was sterilized in an autoclave for 15 minutes at 121° C.

Glycosylated Minimum Agar (GMA)

7.5 g of agar was dissolved into 465 mL of distilled water, and then the solution was sterilized in an autoclave for 15 minutes at 121° C.

Subsequently, a sterile laminar flow, 10 mL of VB, and 25 mL of 40% glucose were added.

Top Agar 0.5 g of sodium chloride and 0.6 g of agar were dissolved into 100 mL of distilled water. The solution was sterilized in an autoclave for 15 minutes at 121° C.

0.05 mM biotin/histidine solution (10 mL/100 mL of top agar)

0.00123 g of biotin and 0.00096 g of histidine were dissolved into 10 mL of distilled water. The solution was sterilized in an autoclave for 15 minutes at 121° C.

Oxoid nutrient broth n. 2.

0.75 g of Oxoid medium was dissolved into 30 mL of distilled water. The solution was sterilized in an autoclave for 15 minutes at 121° C.

Positive and Negative Controls

The negative control is the solvent used to dissolve the sample, using as a standard volume, the highest volume of the tested sample 100 µL, which is also the amount that is required to dissolve the maximum used concentration of the drug.

The positive controls are mutagenic compounds specific for each strain and test condition, with 25 µL/plate of sodium azide (1.25 µg/plate) and 100 µL of mitomycin (0.5 µg/plate) being the controls for TA100 and TA102, respectively, in the absence of metabolic activation. For assays with metabolic activation, the positive control for TA100 is 50 µL 2-antramine (1.25 µg/plate) and for TA102 it is 50 µL 2-aminofluorene (1.25 µg/plate).

Assay Procedure without Metabolic Activation System (−S9)

The preincubation method was used.

$1^{th}$ Day

All solutions and culture media previously described were prepared. In laminar flow, 10 mL of VB solution and 25 mL of 40% glucose solution (previously prepared) were added to the sterile material (GMA), followed by homogenization, and about 25 mL of AMG were distributed to each plate.

The GMA distributed to the plates was left under rest for 48 hours in an oven at 37° C. for subsequent use.

2$^{th}$ Day

In laminar flow, *Salmonella typhimurium* (TA100 and TA 102) strains were inoculated individually with a platinum loop, in the respective nutrient broths and maintained at 37° C., under constant stirring (160 rpm) during 14 hours, in order to achieve a density of 1 to 2×10$^9$ bacteria/mL.

3$^{th}$ Day

Different concentrations of the compounds were added into 100 µL of 0.2M phosphate buffer pH 7.4 (or 500 µL of the mixture S9 in metabolic activation assays) and incubated for 20-30 minutes at 37° C. Solutions containing the compounds had DMSO as the solvent. Thereafter, 2 mL of top agar supplemented with traces of histidine and biotin was added, homogenized and plated in glycosylated minimum medium. After solidification of the top agar, the plates were incubated for 48 hours at a 37° C. Then, the counting of the number of revertant colonies per plate was performed. All tested concentrations, positive and negative controls were run in triplicate.

5$^{th}$ Day

After 48 hours, the revertant colonies were counted manually, and the protoCOL Colony Counter Version 3.15.630 (1998-2001) SYNBIOSIS LTD system was used for the positive control.

Evaluating and Interpreting the Results

The final data obtained from the assay was analyzed using the statistical software Salanal (Salmonella Assay Analysis) version 1.0 from the Research Triangle Institute, RTP, North Carolina, USA. Such software allows the dose-response effect to be evaluated by means of analysis of variance (ANOVA—test F) computations between the measurement of the number of revertants at the different tested concentrations (doses) and the negative control, followed by a linear regression. The software model chosen for analyzing the data was Bernstein's (BERNSTEIN, L. et al. Mutat. Res. v. 97, p. 267-281, 1982.). The slope of the straight line from the linear portion of the dose-response curve is also provided by this software and corresponds to the number of revertants induced per measurement unit of the analyzed sample.

From the results, the mutagenicity ratio (MR) was computed for each analyzed dose from each compound. MR is given by the following equation:

MR=average number of revertants Per test plate(spontaneous+induced revertants)

average number of revertants per plate of the negative control (spontaneous revertants)

The spontaneous growing means that the number of revertants which developed on the plate, regardless of being induced or not, wherein values higher or equal to 2 are considered as a positive response (VALENT, G. V. et al. Env. Toxicol. Water Quality. v. 8, p. 371-381, 1993.).

Assay Procedure with Metabolic Activation System (+S9)

The mutagenicity test with metabolic activation system was performed with a microsomal fraction S9 (S9 mix) prepared from a liver homogenizate from Sprague Dawley rats, previously treated with Aroclor 1254, acquired in the freeze-dried form.

50 mL of S9 mix were prepared using the following solutions shown in Table 7 below:

TABLE 7

Solutions used for the preparation of S9 mix.

| | |
|---|---|
| Sterile water | 19.75 mL |
| Phosphate buffer 0.2M | 25 mL |
| NADP 0.1M | 2 mL (freezer) |
| G-6-P 1M | 250 µL (refrigerator) |
| MgCl 0.4M | 500 µL (refrigerator) |
| KCl 1.65M | 500 µL |
| S9 Fraction | Dissolved into 2 mL of sterile miliQ water |

The procedure for this assay is the same, however, instead of the buffer, 500 µL of the S9 mixture should be added.

The S9 mixture has a viability of 4 hours from preparation when put on ice. The plates are then incubated for 48 hours at 37° C. After the required time has elapsed, the counting of the revertant colonies was carried out. All tested concentrations, positive and negative controls were run in triplicate.

Procedures for Assay in K562 Cell Culture

The human leukemia cell line K562 ATCC (American Type Culture Collection), Philadelphia, Pa., USA was used. The cells were cultured in DMEM medium (Dulbecco's Modified Eagle Medium, Invitrogen, USA) containing 10% of fetal bovine serum and glutamine. The cells were maintained at 37° C. under a 5% $CO_2$ atmosphere. For the experiments, the cells were incubated at a density of 1×10$^5$ cells/mL. In order to carry out the culture with hemin (30 uM), it was added 72 hours before the beginning of the experiment with the desired compound.

The 0-hour time consisted in removing non-treated K562 cells. From this point, the respective compounds were added at the desired concentrations (5, 30, 60 and 100 uM), the cells were then maintained for 7 days under culture, without a new addition of any compound or substitution of the culture medium. Cell collections were performed at the following times: 0, 24, 48, 72 and 96 hours. The morphology of the cells was analyzed at these points through cytospin slides stained with Leishman and the cell viability was performed by staining with trypan blue in a Neuberger's chamber.

RNA Extraction

The extraction method with TRIzol reagent (Gibco-BRL, Gaithersburg, Md.) according to the manufacturer's instructions was used in order to obtain the RNA from K562. The sample containing K562 and TRIzol was incubated for 5 minutes at room temperature in order to achieve complete dissociation of the nucleoproteic complexes, 200 µL of chloroform ($CHCl_3$) was added and thoroughly stirred, and incubation was again performed by 5 minutes at room temperature. After centrifugation for 15 minutes at 19,000 g at a temperature of 4° C., the supernatant was obtained and stored in another tube, proceeding immediately to the step of precipitation with 500 µL of cold isopropanol. After homogenization, a new incubation was carried out for 10 minutes at room temperature, followed by centrifugation for 10 minutes at 19,000 g at 4° C. The supernatant was disposed of and 800 µL of 70% cold ethanol was added to the precipitate, with a new centrifugation being carried out for 5 minutes at 14,000 at 4° C. Finally, the supernatant was disposed of and the RNA precipitate was left to dry for 10 minutes at room temperature, and then resuspended in sterile water containing diethyl pyrocarbonate (DEPC) and incubated at 55° C. for 10 minutes and subsequently put on ice for total solubilization of the RNA.

The sample was checked as to its integrity by electrophoresis on a 1.2% denaturing agarose gel. The samples having a suitable amount of RNA showed integrity on both ribosomal subunits: 18S e 28S. After electrophoresis, the RNA samples were stored in a freezer at −80° C.

Complementary DNA (cDNA) Synthesis

The RNA samples obtained were subjected to the complementary DNA (cDNA) synthesis using the Superscript III RT™ kit (Invitrogen, Life Technologies). After reading in a spectrophotometer (Gene Quant-Pharmacia, USA) and quantification, 3 µg of RNA were treated with the enzyme DNase I (Invitrogen, Life Technologies), for removal of contaminant DNA. 1.0 µL of 1 u/µL DNase I, 1.0 µL of 10× DNase I Reaction Buffer (200 mM Tris-HCl, 20 mM MgCl2, 500 mM KCl2) and water sufficient for a final volume of 10.0 µL of reaction were added. The reaction was carried out for 15 minutes at room temperature and stopped with 1.0 µL of 25 mM EDTA, and incubated for 10 minutes at 65° C.

For cDNA synthesis, 1.0 µL of 50 µM oligo (dT) 20 and 1.0 µL of 10 mM dNTP's were then added. The samples were incubated for 5 minutes at 65° C., followed by 1 minute at 4° C. To each sample, 10.0 µL of the following reaction mixture were added: 2 µL of 10×RT buffer, 4.0 µL of 25 mM MgCl2, 2.0 µL of 0.1 M DTT, 1.0 µL of 40 U/µL RNase OUT™ and 1.0 µL of 200 U/µL Superscript III RT™. The reaction occurred for 50 minutes at 50° C., followed by 5 minutes at 85° C. Thereafter, 1.0 µL of 2 U/µL E. coli RNase H was added for 20 minutes at 37° C.

Verification of Complementary DNA Synthesis

The verification of cDNA synthesis was made by means of PCR for amplification of the beta-actin (BAC) gene. Reactions were carried out with: 5.0 µL of 10×PCR buffer (20 mM Tris-HCl, 500 mM KCl), 1.5 µL of 50 mM MgCl2, 1.0 µL of 10 mM dNTP's, 1.0 µL of 10 mM of BACF primer (5"-AAGAGATGGCCACGGCTGCT-3"), 1.0 µL of 10 mM of BACR primer (5"-TCGCTCCAACCGACTGCTGT-3"), 0.5 µL of Taq DNA polymerase, 1.0 µL of cDNA and 39 µL of water, for a final volume of 50 µL. The program was started for 2 minutes at 94° C., followed by 35 cycles: 94° C./30 seconds-58° C./45 seconds-72° C./40 seconds, being terminated by 72° C./7 minutes. The products were subjected to electrophoresis on 1% agarose gel to verify the amplification of 640 pb.

Design of Primers for Quantitative Real-Time PCR Reaction

The primers used in Quantitative Real-Time PCR reactions were designed with the software "Primer Express" (Applied Biosystems), analyzed in the program Blast (www.ncbi.nlm.nih.gov/blast) to verify the conditions for formation of structures, such as hairpins and dimers.

Standardizations Required for Quantitative Real-Time PCR

Primer Concentration

The optimum concentration of primer to be used in quantitative real-time PCR should be sufficiently low to allow duplication of all copies of the gene present in the sample. Using the same amount of sample, reactions containing each of the primers (sense and antisense) were performed at the final concentration of 150 nM, 300 nM, 600 nM e 900 nM. The cycle in which fluorescence is detected above the established threshold is called threshold cycle or Tc. Since the same amount of sample was used in all reactions, the Tc should not change. If the increase on the primer concentration caused a reduction in Tc, so the amount of this reagent in the reaction was still insufficient. Thus, the optimum concentration chosen was the minimum, associated with the lower Tc.

The sequence and length of the amplified fragments from each primer pair used in the amplification of the genes studied in the quantitative real-time PCR technique is shown in table 8.

TABLE 8

Sequence and length of the amplified fragments

| Gene | Primer Sequence | Length of the amplified fragment |
|---|---|---|
| Gamma-Glob-F | 5'-CCAGCTGAGTGAACTGCACTGT-3' | 81 bp |
| Gamma-Glob-R | 5'-ACGGTCACCAGCACATTTCC-3' | |
| β-actin-F | 5'-AGGCCAACCGCGAGAAG-3' | 79 bp |
| β-actin-R | 5'-ACAGCCTGGATAGCAACGTACA-3' | |
| GAPDH-F | 5'-GCACCGTCAAGGCTGAGAAC-3' | 89 bp |
| GAPDH-R | 5'-CCACTTGATTTTGGAGGGATCT-3' | |

The primer concentrations used in the amplification of the studied genes and the amplification efficiency obtained is shown in Table 9. The concentrations were defined by the amplification efficiency generated under the tested conditions.

TABLE 9

Primer concentrations

| Primer | Used concentration | Primer efficiency |
|---|---|---|
| Gamma-glob | 150 nM | 100% |
| β-actin | 300 nM | 100% |
| GAPDH | 300 nM | 100% |

Reaction Efficiency

In order that the real-time PCR reaction is reliable and reproducible, optimum reaction conditions are required, i.e., the amplifications must show 100% amplification efficiency at every cycle, occurring sample duplication. The amplification efficiency is obtained from formula 10 (−1/slope), wherein slope means the slope value of the curve. Optimization occurs using the optimum primer concentration with 7 known sample amounts, in logarithmic scale: 2 ng (2×100), 6.32 ng (2×100.5), 20 ng (2×10$^1$), 63.2 ng (2×101.5), 120 ng, 200 ng (2×102) e 632 ng (2×102.5). The results are used to construct a standard curve Tc versus sample amount.

Quantitative Real-Time PCR

After reading in a spectrophotometer (Gene Quant-Pharmacia, USA) and quantification, cDNA aliquots were used as template in quantitative real-time PCR reactions. The technique consists in optically monitoring the fluorescence emitted during the PCR reaction, by means of the binding of a specific probe or dye to the newly synthesized strand.

The reactions, always run in duplicate, were performed using the reagent SYBERGreen PCR Master Mix® (Applied Biosystems), which in addition to containing all reagents required for PCR (dNTP's, MgCL2, buffer, Taq Ampli-Gold), also contains the SYBERGreen dye, a double-stranded intercalating agent necessary for the detection of the reaction from cycle to cycle. Further, cDNA samples and specific primers for the analyzed gene were used.

The real-time amplification detection was performed in the apparatus ABI 5700 Sequence Detector System® (Applied Biosystems) in fluorescence versus cycle number graphs. The higher the expression of a gene, that is, the more copies there are at the beginning of the reaction, the earlier will occur amplification, and hence, the lower will be the Tc.

The reactions carried out contained 12.5 μL of the reagent SYBERGreen PCR Master Mix®, 25 ng of cDNA sample and the optimum determined primer concentration, making up a final volume of 25 μL. In all cases, negative controls were made containing sterile water in place of the sample. The reactions were prepared in 96-well plates (Sorenson, BioScience Inc) with plastic caps which allow the passage of light. The program was started at 95° C./10 minutes, followed by 45 cycles: 95° C./15 seconds-60° C./1 minute. At the end of a normal amplification, a degradation step is added during which the temperature rises gradually from 60° C. to 95° C. As the products generated by PCR denaturate with the temperature rise, the florescence signal of SYBR Green decreases. The resulting graph allows verifying if there is one or more PCR products present in each reaction, due to melting temperature differences between amplified PCR products, this difference being caused by the number and composition of bases of each product.

Analysis of Real-Time Data

The expression of the genes of interest was determined in a relative way, being normalized with respect to genes called calibrators; in this study, we used β-actin and GAPDH, which are genes whose expression is supposedly constitutive, that is, they show little variation between various conditions. However, some studies have been demonstrating that the expression of these genes may change substantially. From the Tc values obtained, the arithmetic mean of Tc duplicates was computed. Subsequently, the amount of expression (Q) was obtained by means of the formula Q=EdeltaTc, where E=reaction efficiency and delta Tc=lowest Tc observed−Tc of the sample. Thus, the expression was related with the sample which exhibited the highest expression (Lowest Tc observed), which received a value Q=1. The Q values of the calibrator genes of each sample were subjected to the Gnorm program, which computes the geometric mean between the same, which value is called sample Normalization Factor. The normalized expression of a given gene of interest in a certain sample is given by the ration between value Q of the gene of interest of the sample and the sample Normalization Factor. The obtained data is expressed in arbitrary units or absolute expression value.

Abdominal Writhing Assay Induced by Acetic Acid

The antinociceptive profile was evaluated through the abdominal writhing assay induced by acetic acid in mice. In this assay, Swiss mice from both genders were used, weighing from 21 to 28 grams, fasted for a time period of about 8 hours. The test substance was administered orally and had, as a carrier, 5% gum arabic. After 1 hour, the administration of acetic acid 0.1N (0.1 mL/10 g weight) was performed in the peritoneal cavity of the animals. Ten minutes after the injection of acetic acid, writhings were counted during 20 minutes. Controls were made for the carrier (gum arabic) and it does not show pharmacological activity.

Mouse Ear Edema Assay Induced by Capsaicin

This assay was performed using Swiss mice from both genders weighing from 18 to 30 grams. The animals were fasted for 8 hours with free access to water. This assay consists in locally administering (right ear) 20 μl of a capsaicin solution (250 μg/ear) diluted in acetone, 1 hour after the i.p. administration (diluted in 0.5% gum arabic). The left ear (control) received the carrier in which capsaicin was diluted (acetone) and the right ear received capsaicin. This assay is characterized by an acute inflammatory response of the ear, with development of edema. The animals were sacrificed and their ears were weighted to obtain the inflammation index. A biopsy (8 mm in diameter) of the ear was carried out. Next, the weights of the inflamed ears were compared against the weights of the contralateral ear (control ear) which were not treated with the phlogistic agent. The edema inhibition percentage was calculated by subtracting the ear treated with the carrier by that treated with capsaicin from each group of animals treated with the test substances, and then it was divided by the difference between the groups of the irritating agents and the control groups. The result was subtracted by 1 and multiplied by 100, being shown in Table 4.

Peritonitis Assay

The mice were treated with the substances being analyzed or carrier and after 1 h of oral administration, they were simultaneously subjected to the peritonitis assay, by administering intraperitoneally 1 ml of a 3% thioglycolate solution. 4 h after the administration of thioglycolate, the peritoneal cavity was washed with 3 ml of a HANKS solution (Balanced salt solution, free of $Ca^{2+}$ and $Mg^{2+}$). Next, the peritoneal wash was analyzed and the total counting of white blood cells was made in a Newbauer's chamber under an optical microscope with a 40× objective. Results are shown in Table 5.

Statistical Analysis

The significance levels between experimental groups and the control were generated using the Student's T Test. The values were considered significant when *$P \leq 0.05$. Results were expressed as mean±standard error of the mean, as indicated in the legends of figures.

Citotoxicity Assay in Mouse Peritoneal Macrophages

The determination of cell viability (FIG. 5) was performed by suspending peritoneal macrophages in a RPMI solution, set at a concentration of $5 \times 10^6$ cells/mL, 100 μL of which were added to each cavity of 96-cavity tissue culture plates, being incubated with drugs and prodrugs at concentrations of $10^{-4}, 10^{-5}, 10^{-6}, 10^{-7}, 10^{-8}$ mM during 24 hours at 37° C. and 5% of $CO_2$. The absorbance reading was performed in a UV/Visible spectrophotometer at 540 nm with reference filter at 620 nm (Microplate Reader-Model 550-BIORAD).

Obtainment and Culture of Peritoneal Exudate Cells:

Mice were previously inoculated with 3.0 mL of 3% thioglycolate intraperitoneally in order to stimulate the macrophages of this cavity. After 3 days of stimulation, the animals were sacrificed and the peritoneal macrophages collected. The cells were then washed from 2 to 3 times per centrifugation at 358 g (Centrifuge Fanem Excelsa II 206 MP) during 5 minutes in sterile PBS and, then, resuspended in 1 mL of RPMI-1640 for counting in a Neubauer's chamber. After counting, the concentration was set at $5 \times 10^6$ cells/ml and these cells were distributed to disposable sterile plates with 96 cavities. The plates thus containing the suitable concentration of cells were taken to incubation for 24 hours in a oven at 37° C., containing 95% of moisture and 5% of $CO_2$ in the presence of the anti-inflammatory agents and taurine derivatives at the respective concentrations: $10^{-8}, 10^{-7}, 10^{-6}, 10^{-5}$ and $10^{-4}$ mM or even in the presence of the RPMI-1640 medium only. LPS was used as a positive control and the RPMI-1640 medium as a cell control. The culture supernatants, upon the end of the incubation period, were collected in order to determine the nitric oxide levels thereof. The RPMI-1640 used during this whole process was supplemented with 2 mM I-glutamine, penicillin (100 U/ml), streptomycin (100 ug/ml), 5% of bovine fetal serum and 2-mercaptoethanol $5 \times 10^{-2}$ M (RPMI-1640-C).

Nitric Oxide Dosage

Figure 6:
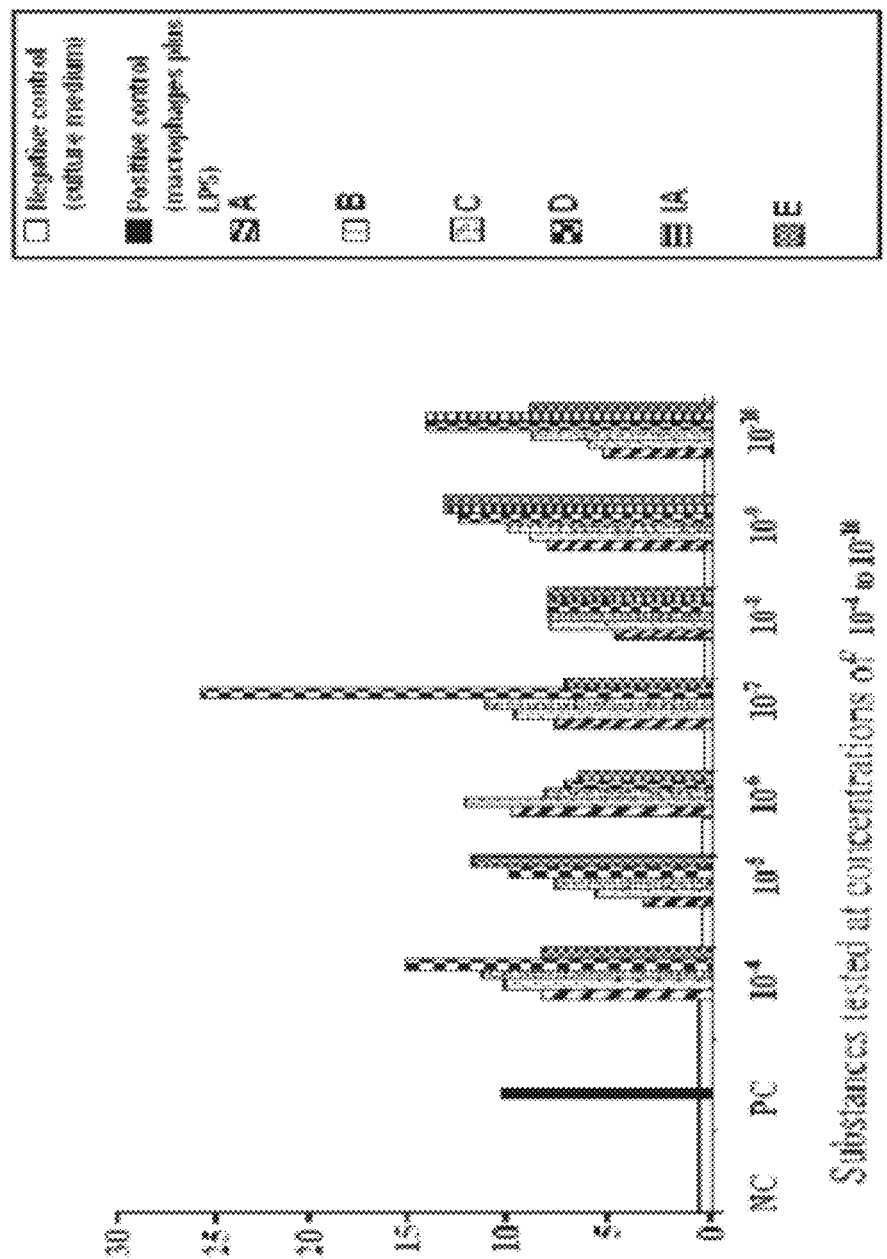
FIG. 6—Dosing of nitric oxide by indirect pathway (nitrite)

After obtaining the supernatants from macrophage cultures, as described above, the concentration of nitric oxide was evaluated. This evaluation was made by measuring the concentration of accumulated nitrite (a stable degradation product of nitric oxide) through a diazotization reaction with the Griess reagent (1% sulfanilamide, 0.1% naphthylenediamine dihydrochloride, in 5% of phosphoric acid), according to the method of Green et al. (1982). To do so, 50 μl of the culture supernatant was incubated with the same volume o Griess reagent at room temperature (10 minutes) and, thereafter, absorbances were measured at 550 nm in a ELISA reader (Microplate Reader-Model 550-BIORAD). Nitrite concentrations were obtained from a standard curve previously prepared with known $NaNO_2$ molar concentrations. The tests were run in triplicate and the values expressed in micromole of $NO^{2-}/5 \times 10^5$ cells. Results are shown in FIG. 6.

The invention claimed is:

1. Compound characterized by being of formula (IE):

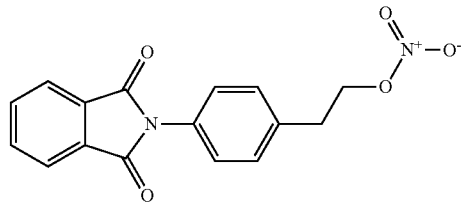

(IE)

* * * * *

SEQUENCE LISTING

```
<160> NUMBER OF SEQ ID NOS: 8

<210> SEQ ID NO 1
<211> LENGTH: 20
<212> TYPE: DNA
<213> ORGANISM: Homo sapiens
<220> FEATURE:
<221> NAME/KEY: source
<222> LOCATION: (1)..(20)
<223> OTHER INFORMATION: Organ: bone marrow; Disease: chronic
      myelogenous leukemia

<400> SEQUENCE: 1
aagagatggc cacggctgct                                              20

<210> SEQ ID NO 2
<211> LENGTH: 20
<212> TYPE: DNA
<213> ORGANISM: Homo sapiens
<220> FEATURE:
<221> NAME/KEY: source
<222> LOCATION: (1)..(20)
<223> OTHER INFORMATION: Organ: bone marrow; Disease: chronic
      myelogenous leukemia

<400> SEQUENCE: 2
tcgctccaac cgactgctgt                                              20

<210> SEQ ID NO 3
<211> LENGTH: 22
<212> TYPE: DNA
<213> ORGANISM: Homo sapiens
<220> FEATURE:
<221> NAME/KEY: source
<222> LOCATION: (1)..(22)
<223> OTHER INFORMATION: Organ: bone marrow; Disease: chronic
      myelogenous leukemia

<400> SEQUENCE: 3
ccagctgagt gaactgcact gt                                           22

<210> SEQ ID NO 4
<211> LENGTH: 20
<212> TYPE: DNA
<213> ORGANISM: Homo sapiens
<220> FEATURE:
<221> NAME/KEY: source
<222> LOCATION: (1)..(20)
<223> OTHER INFORMATION: Organ: bone marrow; Disease: chronic
      myelogenous leukemia

<400> SEQUENCE: 4
acggtcacca gcacatttcc                                              20

<210> SEQ ID NO 5
<211> LENGTH: 17
<212> TYPE: DNA
<213> ORGANISM: Homo sapiens
<220> FEATURE:
<221> NAME/KEY: source
<222> LOCATION: (1)..(17)
```

```
-continued

<223> OTHER INFORMATION: Organ: bone marrow; Disease: chronic
      myelogenous leukemia

<400> SEQUENCE: 5
aggccaaccg cgagaag                                                    17

<210> SEQ ID NO 6
<211> LENGTH: 22
<212> TYPE: DNA
<213> ORGANISM: Homo sapiens
<220> FEATURE:
<221> NAME/KEY: source
<222> LOCATION: (1)..(22)
<223> OTHER INFORMATION: Organ: bone marrow; Disease: chronic
      myelogenous leukemia

<400> SEQUENCE: 6
acagcctgga tagcaacgta ca                                              22

<210> SEQ ID NO 7
<211> LENGTH: 20
<212> TYPE: DNA
<213> ORGANISM: Homo sapiens
<220> FEATURE:
<221> NAME/KEY: source
<222> LOCATION: (1)..(20)
<223> OTHER INFORMATION: Organ: bone marrow; Disease: chronic
      myelogenous leukemia

<400> SEQUENCE: 7
gcaccgtcaa ggctgagaac                                                 20

<210> SEQ ID NO 8
<211> LENGTH: 22
<212> TYPE: DNA
<213> ORGANISM: Homo sapiens
<220> FEATURE:
<221> NAME/KEY: source
<222> LOCATION: (1)..(22)
<223> OTHER INFORMATION: Organ: bone marrow; Disease: chronic
      myelogenous leukemia

<400> SEQUENCE: 8
ccacttgatt ttggagggat ct                                              22
```